United States Patent
Maskiewicz et al.

(10) Patent No.: US 10,207,028 B2
(45) Date of Patent: Feb. 19, 2019

(54) MICROCOMPOSITES FOR TREATMENT OF BONE

(71) Applicant: Loma Linda University, Loma Linda, CA (US)

(72) Inventors: Victoria Maskiewicz, Redlands, CA (US); Gary Botimer, Loma Linda, CA (US); Serkan Inceoglu, Moreno Valley, CA (US)

(73) Assignee: Loma Linda University, Loma Linda, CA (US)

( * ) Notice: Subject to any disclaimer, the term of this patent is extended or adjusted under 35 U.S.C. 154(b) by 82 days.

(21) Appl. No.: 14/500,907

(22) Filed: Sep. 29, 2014

(65) Prior Publication Data

US 2015/0093443 A1 Apr. 2, 2015

Related U.S. Application Data

(60) Provisional application No. 61/883,500, filed on Sep. 27, 2013.

(51) Int. Cl.
| | |
|---|---|
| *A61K 39/395* | (2006.01) |
| *A61L 24/00* | (2006.01) |
| *A61P 35/00* | (2006.01) |
| *C07H 21/00* | (2006.01) |
| *A61L 27/44* | (2006.01) |
| *A61L 27/50* | (2006.01) |
| *A61L 27/54* | (2006.01) |
| *A61L 27/56* | (2006.01) |

(52) U.S. Cl.
CPC .............. *A61L 27/446* (2013.01); *A61L 27/50* (2013.01); *A61L 27/54* (2013.01); *A61L 27/56* (2013.01); *A61L 2300/406* (2013.01); *A61L 2300/414* (2013.01); *A61L 2300/622* (2013.01); *A61L 2400/06* (2013.01); *A61L 2430/02* (2013.01); *A61L 2430/24* (2013.01)

(58) Field of Classification Search
CPC ........ A61L 27/446; A61L 27/50; A61L 27/56; A61L 27/54
See application file for complete search history.

(56) References Cited

U.S. PATENT DOCUMENTS 4,588,583 A * 5/1986 Pietsch ............... A61L 24/0021
514/772.4
4,610,692 A * 9/1986 Eitenmuller ............ A61L 27/12
264/43
2012/0308633 A1  12/2012 Shen et al.

OTHER PUBLICATIONS

Ye et al. (J Mater Sci: Mater Med, Published 2011, pp. 2487-2496).*
Michailidis et al. (Ceramics International 41, 2015, 3822-3832).*
Polymer Database (Poly(methyl acrylate), accessed from http://polymerdatabase.com/polymers/polymethylacrylate.html, accessed on Apr. 24, 2018, pp. 1-2).*
Chemical Book (Calcium phosphate, accessed from https://www.chemicalbook.com/ProductMSDSDetailCB3125692_EN.htm, accessed on Apr. 24, 2018, pp. 1-4).*
Bone Cements: Review of Their Physiochemical and Biochemical Properties in Percutaneous Vertebroplasty, List of cement manufactures and contact information, http://www.ajnr.org/content/25/6/1286/TI.expansion.html, accessed Sep. 11, 2013.
Shen et al.: "Mesoporous silica nanoparticle-functionalized poly(methyl methacrylate)-based bone cement for effective antibiotics delivery," J Mater Sci: Mater Med (2011) 22:2283-2292.
Xie et al.: "Study of Poly(methyl methacrylate-maleic anhydride)/Silica Hybrid Materials," Journal of Applied Polymer Science, vol. 75, 379-383 (2000).
Yang et al.: "Mechanical Properties of Acrylic Bone Cement Containing PMMA-Sio2 Hybrid Sol-Gel Material," 1997 John Wiley & Sons, Inc. CCC 0021-9304/97/020143-12.

* cited by examiner

*Primary Examiner* — Alma Pipic
(74) *Attorney, Agent, or Firm* — Kilpatrick Townsend & Stockton LLP

(57) ABSTRACT

Compositions having a drug-loaded microparticle and bone cement and methods of making such compositions are disclosed. Also disclosed are methods of employing such compositions for the treatment of injected joint spaces and bone disease.

17 Claims, 5 Drawing Sheets

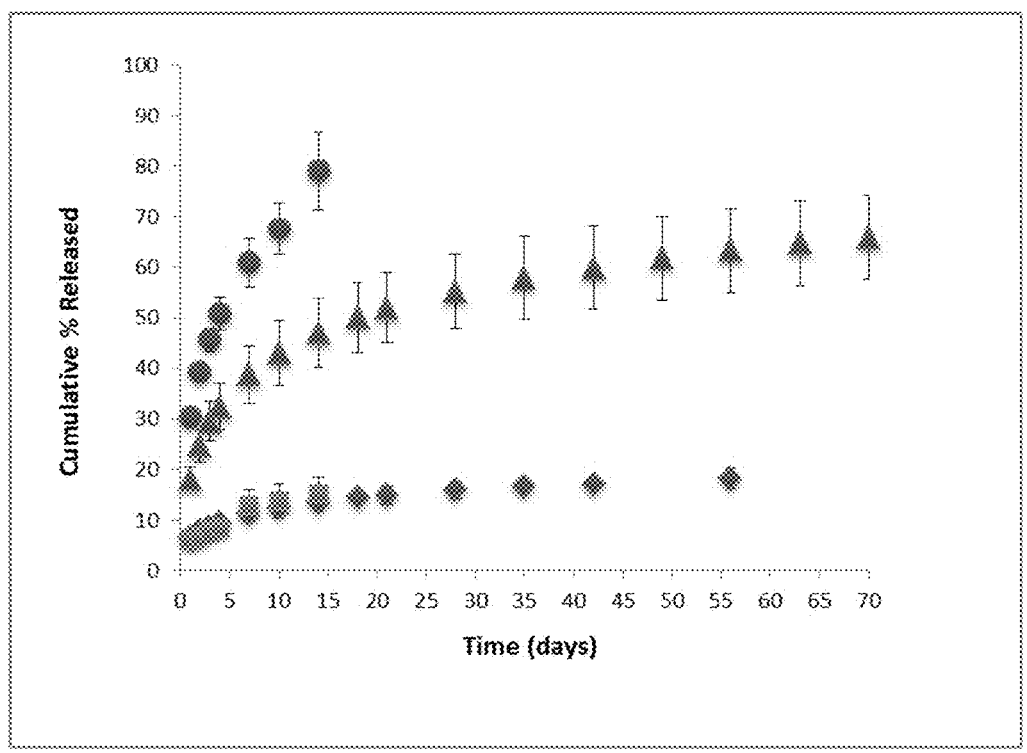

Figure 5: Release of (●) 10% (w/w) gentamicin from microparticle-based PMMA microcomposite rods, (▲) 10% (w/w) vancomycin from microparticle-based PMMA microcomposite rods, (✹) 10% (w/w) gentamicin from PMMA cement (control) rods, and (◆) 10% (w/w) vancomycin from PMMA cement (control) rods. Symbols represent the means of 4 samples; error bars represent the standard deviation surrounding each sample set.

FIGURE 5

MICROCOMPOSITES FOR TREATMENT OF BONE

CROSS-REFERENCE TO RELATED APPLICATIONS

This patent application claims priority to U.S. Provisional Patent Application No. 61/883,500 filed on Sep. 27, 2013, entitled "MICROCOMPOSITES FOR TREATMENT OF BONE", the disclosures of which are herein incorporated by reference in their entirety.

BACKGROUND

Field

The present disclosure relates to methods and compositions for the treatment of infected joint spaces and bone disease.

Description of the Related Art

Infection following total joint replacement is a major complication. National statistics report that 1-2% of all joint replacement procedures fail through infection every year, with an average financial burden of over $80,000 per case, and with the emergence of more resistant strains of bacteria, this cost has been escalating significantly in the past 5 years.

SUMMARY

In one aspect, a composition, comprising a particle comprising at least one drug and a porous solid, wherein the particle is dispersed in a bone cement. In some embodiments, a composition wherein the at least one drug is an antibiotic, a bone growth factor or a chemotherapeutic, or a combination thereof. In some embodiments, a composition wherein the antibiotic is selected from an aminoglycoside antibiotic, a glycopeptide antibiotic, a macrolide antibiotic, fluoroquinolones, sulfa, tetracycline, rifampin, vancomycin, cephalosporin, penicillinc, or a combination thereof. In some embodiments, a composition wherein the antibiotic is gentamicin. In some embodiments, a composition wherein the porous solid comprises a non-erodible particulate system. In some embodiments, a composition wherein the porous solid comprises silica. In some embodiments, a composition wherein the particle has a size of about 2 µm to about 200 µm. In some embodiments, a composition wherein the bone cement is selected from ALLEGIANCE, BONESOURCE, CRANIOPLASTIC, ORTHOCOMP, OSTEOBOND, PALACOS, PALACOS E-FLOW, SIMPLEX P, SUCOUR, and VERTIFIX. In some embodiments, a composition wherein the drug-loading of the particle is about 1% to about 70% by weight of the particle. In some embodiments, a composition wherein the drug-loading of the particle is less than about 40% by weight of the particle. In some embodiments, a composition wherein the weight ratio of particle to bone cement is about 1:9 to about 7:3. In some embodiments, a composition wherein the at least one drug is released over a period of 14 days to 70 days. In some embodiments, a composition wherein 40 percent to 80 percent of the at least one drug is released. In some embodiments, a composition wherein 40 percent of the at least one drug is released over a period of 14 days.

In another aspect, a method of treating a bone condition, comprising locally administering a composition comprising a particle suspended within a bone cement, wherein the particle comprises at least one drug dispersed within a porous solid. In some embodiments, the method of treating a bone condition wherein the bone condition is an infected joint space. In some embodiments, the method of treating a bone condition wherein the at least one drug is selected from an antibiotic, a bone growth factor, or a chemotherapeutic, or a combination thereof. In some embodiments, the method of treating a bone condition wherein the porous solid comprises a non-erodible particulate system. In some embodiments, the method of treating a bone condition wherein the porous solid comprises silica. In some embodiments, the method of treating a bone condition wherein locally administering the composition comprises surgically implanting the composition. In some embodiments, the method of treating a bone condition wherein locally administering the composition comprises injecting the composition. In some embodiments, the method of treating a bone condition wherein the at least one drug is released over a period of 14 days to 70 days. In some embodiments, the method of treating a bone condition wherein 40 percent to 80 percent of the at least one drug is released. In some embodiments, the method of treating a bone condition wherein 40 percent of the at least one drug is released over a period of 14 days.

In another aspect, a method of making a composition comprising a drug-loaded microparticle, the method comprising: combining a porous solid in the form of a microparticle and at least one drug to form a drug-loaded microparticle; combining the drug-loaded microparticle and a bone cement powder to form a powder mixture; adding a monomer to the powder mixture to form a dough; shaping the dough; and curing the dough to form the composition. In some embodiments, the method wherein the porous solid comprises silica. In some embodiments, the method wherein the at least one drug is selected from an antibiotic, a bone growth factor, a chemotherapeutic, or a combination thereof. In some embodiments, the method wherein the bone cement powder is selected from the group consisting of ALLEGIANCE, BONESOURCE, CRANIOPLASTIC, ORTHOCOMP, OSTEOBOND, PALACOS, PALACOS E-FLOW, SIMPLEX P, SUCOUR, and VERTIFIX. In some embodiments, the method wherein the monomer comprises a liquid methacrylate monomer. In some embodiments, the method wherein the at least one drug is released over a period of 14 days to 70 days. In some embodiments, the method wherein 40 percent to 80 percent of the at least one drug is released. In some embodiments, the method wherein 40 percent of the at least one drug is released over a period of 14 days.

In another aspect, a kit for making a composition for treating a bone condition, the kit comprising: a porous microparticle configured to provide extended release of a drug; a bone cement powder; a monomer; and a mold. In some embodiments, the kit wherein the porous microparticle is preloaded with the drug.

BRIEF DESCRIPTION OF THE DRAWINGS

FIG. 5 depicts a graph showing the release of (●) 10% (w/w) gentamicin from microparticle-based PMMA microcomposite rods, (▲) 10% (w/w) vancomycin from microparticle-based PMMA microcomposite rods, (■) 10% (w/w) gentamicin from PMMA cement (control) rods, and (♦) 10% (w/w) vancomycin from PMMA cement (control) rods. Symbols represent the means of 4 samples; error bars represent the standard deviation surrounding each sample set.

DETAILED DESCRIPTION

Figure 1:
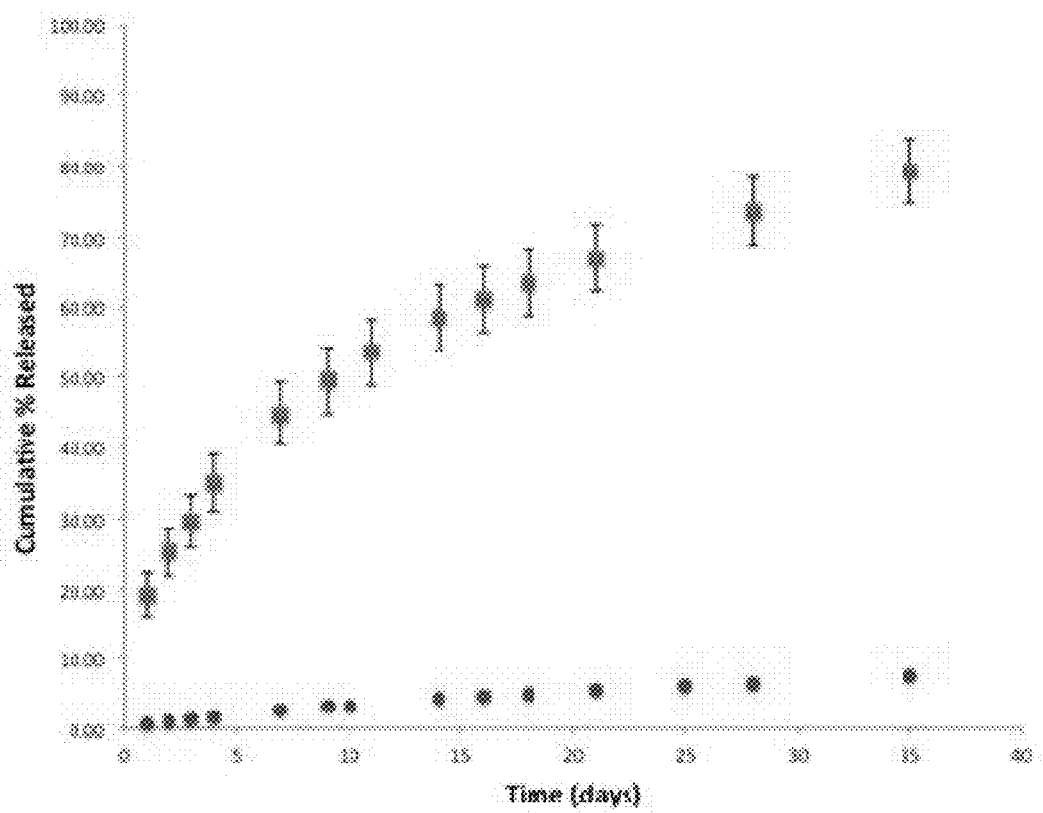
FIG. 1 depicts a graph showing the release of Gentamicin from (●) PMMA cement rods, and (■) microparticle-based PMMA microcomposite rods. Symbols represent the means of 4 samples, bars represent the standard deviations. Note that the standard deviation around the mean release from simple PMMA rods (circles) are small enough to be contained within the symbol.

Infection following total joint replacement is a major complication. National statistics report that 1-2% of all joint replacement procedures fail through infection every year, with an average financial burden of over $80,000 per case, and with the emergence of more resistant strains of bacteria, this cost has been escalating significantly in the past 5 years.

The incidence of periprosthetic infections is 0.5 to 2% and on the rise. It is estimated to be the number one cause of joint revision (25%) and by 2030, it is estimated that 60% of all revisions will be for infection. The cost of treatment runs $60,000 to $200,000 per case. The incidence is related to co-morbidities, two of which, Diabetes Mellitus ("DM") and obesity, are on the rise. In addition, the rise in methicillin-resistant *Staphylococcus aureus* as well as other "super bugs" is making treatment more difficult. All this adds up to a major billion dollar per year burden on the healthcare system.

The standard therapy for infected replacement device is the two-stage exchange revision, which involves the removal of infected components, the implantation of a temporary antibiotic-laden polymeric bone cement spacer, and a minimum 6-week course of intravenous antibiotic therapy to resolve the infection prior to a second surgery (involving the removal of the spacer and the insertion of a revision prosthetic joint). The purpose of the bone cement spacer, which can be custom crafted at the time of surgery or pre-formed commercially, is to provide proper soft-tissue and limb length maintenance between stages and to act as a source of local delivery of antibiotics.

Articulating spacers have been shown to preserve the range of motion of the joint, help maintain cut bone surface, and prevent muscle and ligament contracture and limb shortening. Although the spacers may not be intended or designed for load bearing activities, some minimal mechanical strength may be needed for the spacer to preserve the original geometry and spatial relations of the elements of the joint.

Unfortunately, in order to avoid compromising the mechanical properties of the non-erodible cement spacer, antibiotics are incorporated at very low levels, resulting in the encapsulation of most of the drug deep within the construct and thereby allowing the release of only a small and ineffective fraction of the drug. As a result, sustained drug levels within local tissue do not reach the cytotoxic levels required to clear the infection. The ideal antibiotic-loaded bone cement for management of these infections should release drug such that continuously high antibiotic concentrations over a prolonged period of time are maintained, in order to guarantee infection sanitation and avoid the emergence of new resistant bacterial strains as well as avoid the requirement for sartoid systemic antibiotics at high levels with potential toxicity to the kidneys, liver, and other tissues.

Efforts to improve elution profiles of polymethylmethacrylate ("PMMA") cements by increasing the amount of incorporated antibiotics or by including up to 50% by weight of water-soluble porosigens such as lactose or dextran in the matrix have met little success, and the release profiles of drug remain very similar to those from traditional PMMA cements: an initial burst of drug is released into the surrounding fluid, followed by little to no subsequent release of drug. Moreover, the higher drug and/or porosigen loads incorporated into these cements causes a significant degree of degradation in the mechanical properties of the cement, due to the high porosity that occurs when these porosigens dissolve and elute from the matrix along with the drug.

Shen et al. (U.S. Patent Publication No. 2012/0308633 and Shen et al., Mesoporous Silica Nanoparticle-functionalized Poly(methylmethacrylate)-based Bone Cement for Effective Antibiotics Delivery, J. Mater. Sci.: mater. Med, 22:2283-2292, 2011, both of which are herein incorporated by reference in their entirety) have utilized mesoporous silica nanoparticles with an internal structure of uniformly arrayed, one-dimensional pores to build effective diffusional channels within the PMMA cement in order to facilitate the release of antibiotics.

Shen et al.'s type of bone cement, however, is limited to nanoparticle and nanostructured materials. In order to build and scale up an effective diffusion network for the sustained release of antibiotics from a silica/PMMA composite, Shen et al. disclose that the particle size of the mesoporous silica must be carefully controlled to be in the nanometer range. Shen et al. disclosed that samples formulated with silica with particle sizes above the nano-scale, specifically silica particles with a diameter greater than 0.5 µm to about tens of micrometers, did not release antibiotics effectively because larger particles could not build up an effective diffusion network while formulations with silica having the smallest particle sizes (e.g. in the nanometer range) exhibited the highest drug release rate. Additionally, the release of antibiotics from this system was achieved via the nanoparticles themselves possessing a uniformly arranged pore structure of hexagonal channels or cubic pores which then were loaded with drug. Such nanostructured materials require complex, cumbersome and expensive manufacturing processes of unknown reproducibility, and their synthesis is mediated by fluorocarbon surfactants, which are considered a significant environmental problem. Finally, the delivery of antibiotics from these devices is low, taking over 80 days to release 70% of the drug payload. Many prosthetic joint infections are biofilm associated, and these types of infections are 10 to 1000 times more resistant to the effects of antimicrobial agents than typical planktonic bacteria. As such, these types of bacteria require a significantly greater release rates of antibiotics into the tissues, in order to achieve bacteriostatic/bacteriocidal concentrations, than can be achieved using the nanostructured cement matrix employed by Shen et al. Therefore, a composite that can release higher concentrations of drug in a shorter time span would have significant advantages in the treatment of these infections.

The mechanical properties of inorganic/organic composites, such as silica/polymer hybrid materials, may depend upon the proportion of filler/polymer, the degree of dispersion of filler particles, and the adhesion between the two phases. For these composites, a coupling agent, such as tetraethoxysilane or 3-aminopropyltriethoxysilane, may be used to ensure a good adhesion between phases and improve the dispersion of silica within the polymeric matrix. Unfortunately, these agents have unknown toxicities and as such are not acceptable for use in implants designed for human use. Moreover, the use of pure silica/polymer composites (i.e., those with no coupling agent) is discouraged based on the physicochemical incompatibility between the inorganic and organic species, which may result in decreased tensile strength. For example, Xie et al., Study of Poly(methyl methacrylate-maleic anhydride)/Silica Hybrid Materials, J. Appl. Polym. Sci, 75:379-383, 2000, herein incorporated by reference in its entirety, determined that silica/PMMA composites had lower tensile strengths than the polymer or composites containing coupling agents. Yang et al., Mechanical Properties of acrylic Bone Cement Containing PMMA-SiO2 Hybrid Sol-Gel Material, J. Biomed. Mater. Res. 38:143-154, 1997, herein incorporated by reference in its entirety, similarly reported that the tensile strength of silica/PMMA composites decreased with increasing silica content.

Disclosed herein are methods and compositions for the treatment of bone disease. Methods of making such compositions are also disclosed. Such compositions may include bone cement formulations that are simple, compositionally robust, cost-effective, microstructured materials. In some embodiments, the compositions may be bone cement formulations with non-erodible, drug-containing, microparticulate materials. In some embodiments, the compositions may include a bone cement and a non-erodible, micro-structured material with a random, fractal pore structure into which drug has been embedded. Additionally, the disclosed compositions may be made via simpler manufacturing processes without the need for "environmentally-unfriendly" chemicals, such as fluorinated surfactants.

The disclosed compositions may be an improvement over existing therapies by increasing the rate and extent of drug release. In some embodiments, these compositions may achieve high and sustained release of drugs, including but not limited to antibiotics, from bone cement (such as PMMA-based cement spacers) into infected areas, including but not limited to joint spaces. These compositions include drug-loaded microparticles that may provide geometrically simple, random, non-arrayed, fractal channels to allow sustained release of drug at high rates. Such compositions may overcome the limitation of low drug release from typical commercial bone cements (less than 10% after 30 days), allowing for over 70% of total incorporated drug release in 30 days. In some embodiments, the compositions may exhibit an improved antibiotic elution. Thus, the disclosed compositions may allow for a more advantageous release profile of therapeutic drug (more drug released in a shorter time span) for use in treating infected total joints and osteomyelitis.

Furthermore, in some embodiments, the disclosed compositions may maintain adequate mechanical strength of the cement over the time-course of drug elution. In some embodiments, the disclosed compositions may be an improvement over existing compositions by allowing reproducible assembly from simple components, without the need for ordered, and thereby complex, nanostructured systems. The cement of such compositions may also exhibit mechanical properties sufficient to maintain proper soft-tissue and limb length. One skilled in the art will appreciate that there is no clear and proven definition of the mechanical properties needed for optimal spacer material because of the complex physiological loading pattern of the joints and patient-specific variability. Comparative controlled studies may be preferred as a standard for testing cement formulations using materials known to work in vivo as a control group.

Methods disclosed herein include the use of the disclosed compositions for the localized delivery of a drug and/or other active components. In some embodiments, the disclosed methods relate to the treatment of infected joint spaces. Some methods described herein are directed to the treatment of bone disease.

Compositions

Some embodiments disclosed herein provide for compositions that may include a drug-loaded microparticle having at least one drug and a porous solid and bone cement.

In some embodiments, the drug may include antimicrobials (such as antibiotics), bone growth factors, chemotherapeutics, or any suitable biologically-active agent useful in treating an infection at the implant site, or a combination thereof. Examples of biologically-active agents include but are not limited to antiparasitic agents (such as quinacrine, chloroquine, quinine, and the like), antifungal agents (such as nystatin, amphotericin, miconazole, tolnaflate, undecyclic acid and its pharmaceutically acceptable salts, and the like), antiviral agents (such as vidarabine, acyclovir, ribarivin, amatine hydrochloride, iododeoxyuridine, dideoxyuridine, interferons, and the like). An antibiotic may include but is not limited to an aminoglycoside antibiotic, a glycopeptide antibiotic, a macrolide antibiotic, fluoroquinolones (such as ciprofloxacin, levofloxacin, and moxifloxacin), sulfa (trimethoprim sulfamethoxazole), tetracycline, rifampin, vancomycin, cephalosporins, penicillins, and a combination thereof. In some variations, the antibiotic may be gentamicin. Examples of bone growth factors include but are not limited to insulin-like growth factors, transforming growth factors-$\beta$, and bone morphogenetic proteins. Chemotherapeutics can include any anti-cancer agent, including but not limited to alkylating agents, antimetabolites, anthracyclines, taxes, camptothecins, platinums, and the like.

The porous solid may include silica microparticles. The silica microparticles may, for example, have a mean particle size of about 1 µm to about 200 µm, about 2 µm to about 200 µm, about 2 µm to about 150 µm, about 5 µm to about 100 µm, about 2 µm to about 50 µm, or about 5 µm to about 50 µm. In some embodiments, the silica microparticles may have a mean particle size of less than 100 µm, less than 50 µm, less than 25 µm, or less than 10 µm. In some embodiments, the silica microparticles may have a mean particle size of greater than 1 µm, greater than 5 µm, greater than 10 µm, or greater than 15 µm. In some embodiments, the silica microparticles may be commercially available, such as Sipernat 50s silica microparticles.

In some embodiments, the porous solid may include other non-erodible (non-biodegradable) particulate systems such as porous microparticles comprised of poly(D,L-lactic) acid, polystyrene, ethylene, vinyl acetate, poly(ethylene terephthalate), polyanhydrides, polyorthoesters, polyamides, polycarbonates, polyalkylenes such as polyethylene and polypropylene, polyalkylene oxides such as poly(ethylene oxide), polyalkylene terephthalates such as poly(ethylene terephthalate), polyvinyl ethers, polyvinyl esters, polyvinyl halides such as poly(vinyl chloride), polyurethanes and co-polymers thereof, derivativized celluloses such as alkyl cellulose, hydroxyalkyl celluloses, cellulose ethers, cellulose esters, nitro celluloses, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, and cellulose sulphate sodium salt (jointly referred to herein as "synthetic celluloses"), polymers of acrylic acid, methacrylic acid or copolymers or derivatives thereof including esters, poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate) (jointly referred to herein as "polyacrylic acids"), poly(butyric acid), poly(valeric acid), and poly(lactide-co-caprolactone), copolymers and blends thereof.

Additionally, porous ceramics may be utilized. Exemplary porous ceramics may include, but are not limited to, metal oxides (alumina, magnesia, zirconia etc.), metal phosphates (such as manganese, titanium, iron etc.), and metal carbides (such as silica, calcium, titanium, aluminum etc.).

In some embodiments, the drug-loaded microparticle has a size of about 0.1 µm to about 220 µm, about 2 µm to about 200 µm, about 5 µm to about 150 µm, about 5 µm to about 100 µm, about 2 µm to about 50 µm, or about 2 µm to about 25 µm. In some embodiments, the drug-loaded microparticle may have a drug-loading of about 1% to about 70%, about 10% to about 60%, about 20% to about 50%, or about 30% to about 40% by weight (weight of drug to weight of the drug-loaded microparticle). In some embodiments, the drug-loading of the microparticle is at least about 10%, at least about 20%, at least about 30%, at least about 40%, or at least about 50% by weight. In some embodiments, the drug-loading of the microparticle is less than about 60%, less than about 50%, or less than about 40% by weight. In some embodiments, the drug-loading of the microparticle may be about 50% by weight. In some embodiments, the drug-loaded microparticle may be non-erodible and/or microstructured. The drug-loaded microparticle may also have a random, fractal pore structure into which the drug is embedded.

In some embodiments, the bone cement may include any known bone cement, including those that are commercially available. For example, the following commercially available bone cements may be used: ALLEGIANCE® from Cardinal Health, BONESOURCE™ from Stryker Leibinger, CRANIOPLASTIC™ from Depuy International, ORTHOCOMP™ from Orthovita, OSTEOBOND® from Zimmer, PALACOS® from E. Merck, PALACOS® E-flow from Essex Chemie AG, SIMPLEX® from Stryker, Sucour from ArthroCare, and VERTIFIX® from WE Cook. The physiochemical and biochemical properties of such bone cements are described in Provenzano et al., Bone Cements: Review of Their Physiochemical and Biochemical Properties in Percutaneous Vertebroplasty, American Journal of Neuroradiology, 25: 1286-1290, 2004, herein incorporated by reference in its entirety.

Some embodiments disclosed herein provide for compositions having a drug-loaded microparticle dispersed in the bone cement. The drug-loaded microparticles and bone cement may be separate entities in such compositions, and in some embodiments, the drug-loaded microparticles may be dispersed within the polymeric matrix of the bone cement. A discrete boundary may exist between the polymeric matrix and the drug-loaded microparticles.

In some embodiments, the composition may have a weight ratio of drug-loaded microparticle to bone cement ranging from about 1:9 to about 7:3, or about 1:2 to about 1:3.

In some embodiments, the compositions may have a drug-loading of about 1% to about 50%, about 5% to about 45%, or about 10% to about 40% by weight (weight of drug to weight of the composition). In some embodiments, the drug-loading of the composition is at least about 1%, at least about 5%, or at least about 15% by weight. In some embodiments, the drug-loading of the composition is less than about 50%, less than about 45%, less than about 40%, or less than about 35% by weight.

Methods of Making Compositions

Some embodiments disclosed herein provide for methods of making the disclosed compositions, which include a drug-loaded microparticle and bone cement. In some variations, the method may include combining a porous solid and at least one drug to form a drug-loaded microparticle, combining the drug-loaded microparticle and a bone cement powder to form a powder mixture, adding a monomer to the powder mixture to form a dough, shaping the dough, and curing the dough to form the composition.

Combining a porous solid and at least one drug to form a drug-loaded microparticle may include mixing the drug and the porous solid together. Known methods of mixing such compounds may be used. For example, the drug may be dissolved in a solvent (such as an aqueous solution, organic solvent, or mixture thereof), and to this solution, the porous solid may be added. In some embodiments, the porous solid may be dissolved in a solvent, and to this aqueous solution, the drug may be added. In some embodiments, the drug and porous solid may first be combined, and the mixture may then be subsequently dissolved in a solvent.

One of ordinary skill will appreciate that solutions of drug may need to be titrated such that the concentration of drug is maximized without exceeding its solubility and enough liquid volume is maintained to fully wet the silica (or other) porous microparticles. Thus, the concentration of drug in solution may vary depending on, for example, the solubility of the drug. As a non-limiting example, when loading 4 gm gentamicin sulfate (aqueous solubility 50 mg/mL), the drug may be dissolved in 80 mL nanopure water until a clear, yellow solution is formed. Then the microparticles (4 gm) may be added to form a thin paste. After an hour of equilibration, the liquid is removed by lyophilization or vacuum drying. Note that if a very aqueous soluble drug were used such that only 2 mL of water were needed to dissolve the drug, this volume of solution may be increased to the minimum needed to wet 4 gm of silica microparticles (about 8-10 mL) to form a paste, equilibrated for at least 30 minutes and less than 24 hours, and removed to form the drug-loaded microparticle powder.

The mixture of the drug and porous solid may be maintained, either with or without stirring, at about 5° C. to about 85° C., about 10° C. to about 70° C., or about 20° C. to about 55° C. In some embodiments, the mixture of the drug and porous solid may be maintained at about room temperature. The mixture may be maintained at these appropriate temperatures from about 15 minutes to about 26 hours, about 20 minutes to about 25 hours, or about 30 minutes to about 24 hours. The solvent may subsequently be removed according to known methods, e.g. via vacuum, filtration, lyophilization, and the like. The resultant powder may be further purified to remove any aggregates via known methods, such as by sieving the powder through a mesh, thereby yielding the drug-loaded microparticles.

Combining the drug-loaded microparticle and a bone cement powder to form a powder mixture may include mixing the drug-loaded microparticle with a bone cement powder. In some embodiments, the bone cement powder may be commercially available, such as ALLEGIANCE® from Cardinal Health, BONESOURCE™ from Stryker Leibinger, CRANIOPLASTIC™ from Depuy International, ORTHOCOMP™ from Orthovita, OSTEOBOND® from Zimmer, PALACOS® from E. Merck, PALACOS® E-flow from Essex Chemie AG, SIMPLEX® P from Stryker, Sucour from ArthroCare, and VERTIFIX® from WE Cook, and the like. In some embodiments, the powder mixture may have about 10% to about 70% of drug-loaded microparticle, about 20% to about 80% of drug-loaded microparticle, or about 30% to about 50% by weight of drug-loaded microparticle. In some embodiments, the powder mixture may have at least about 20% of drug-loaded microparticle, at least about 30% of drug-loaded microparticle, at least about 40% of drug-loaded microparticle, or at least about 50% by weight of drug-loaded microparticle. In some embodiments, the powder mixture may have less than about 70% of drug-loaded microparticle, less than about 60% of drug-loaded microparticle, or less than about 50% by weight of drug-loaded microparticle.

Adding a monomer to the powder mixture to form a dough may be carried out according to known methods. In some embodiments, the monomer may be a liquid solution, such as liquid methacrylate. In some embodiments, the bone cement powder and monomer may be commercially available as one product.

Shaping the dough may be carried out via known methods, such as by pressing the dough into an appropriately shaped mold. The dough may be formed into any shape, including but not limited to spheres, blocks, rounded rods, and rectangular rods. The dough, in some variations, may be shaped into varying size and the shapes may vary in size from each other or may all be the same size. The dough may be shaped into an anatomical shape. In some embodiments, the dough may be shaped into a size appropriate for its application. As non-limiting examples, the dough may be as small as a bead for use in small spaces or may be as large as necessary for use in large joints, such as a hip joint.

Curing the dough to form the composition may also be carried out according to techniques known to a skilled artisan. The dough may be cured, either with or without stirring, at about 1° C. to about 70° C., about 3° C. to about 65° C., or about 5° C. to about 60° C. In some embodiments, curing the dough may be carried out at about room temperature. The dough may be cured for about 10 minutes to about 80 hours, about 20 minutes to about 75 hours, or about 30 minutes to about 72 hours. Curing the dough to form the composition may be carried out until a hardened form is achieved. In some embodiments a polymerization initiator may be included to modulate the time of curing. In other embodiments, photopolymerization (e.g., using UV light) may be used to induce curring.

In some embodiments, at least part of the method could be carried out before the composition is sold or provided for use in the surgical suite, for example, the loading of a drug into the drug-loaded particles. The loading of the drug into the drug loaded particle may be carried out by mixing a solution of a drug with silica particles to form a paste or suspension, and subsequently removing the liquid by lyophilization, or evaporation to form a dry powder. The dry powder may comprise drug-loaded particles that can achieve the desired release rates as described herein. In some embodiments, the composition can be provided as a finished spacer product. For example, the steps of adding a liquid monomer to form a dough and shaping and/or curing the dough can be carried out prior to providing the finished spacer product for use. In other embodiments, the drug-loaded particle can be provided as the product and the steps required for formation of the finished spacer product are performed in the surgical suite. These steps can include combining the drug-loaded particle with the bone cement to form a powder phase, and adding a liquid monomer to the powder to form a dough, and subsequently the intended implant. Additionally, in some embodiments, the molding and curing of the dough can be performed in the surgical suite.

A kit can be provided that contains the materials and methods for forming a finished spacer product. The kit can provide a porous solid or any other solid particle as described herein, and in some embodiments, at least one drug. The porous solid can be combined with the at least one drug in solution. After equilibration (e.g., for about 0.2, 0.4. 0.6, 0.8, 1, 2, 3, 4, 5, 6, 12, 24 or 48 hours), the liquid is removed by lyophilization, vacuum drying, evaporation, or other technique known in the art. Further, a bone cement powder can be provided in the kit to form a powder mixture by mixing the drug-loaded microparticle with the bone cement powder. A monomer can be included in the kit and combined with the powder mixture to form a dough. The combination of the monomer and the powder mixture may be carried out according to known methods. A shape mold can be contained in a kit to shape the dough through known methods, such as by pressing the dough into an appropriately shaped mold and allowing the dough to cure. With the methods and materials in the kit, the finished spacer product can be made to be used by a medical professional. In some embodiments, the kit further comprises instructions for preparing the implant. In some embodiments, the components of the kit a packaged and pre-sterilized.

Alternatively, in some embodiments, a kit could be provided to prepare the finished product including a drug-loaded particle prefabricated to contain a porous solid and at least one drug prepared utilizing the methods as described herein. The already prepared drug-loaded particle can be provided in the kit with the all or some of the components necessary to prepare the finished spacer product. For example, the kit can include the drug-loaded particle, bone cement, liquid monomer, and a shape mold. The drug-loaded particle can be mixed with bone cement to form a powder phase, and a liquid monomer can be provided and added to the powder to form a dough and, subsequently, the intended implant.

Methods of Treatment

Disclosed herein are methods of treating an infected total joint and osteomyelitis and/or bone disease. The disclosed compositions may be used to treat any infected tissue, including but not limited to soft-tissue, dental tissue, joint spaces, etc. In some embodiments, an infected joint space may be treated by administering within the space a composition comprising a plurality of drug-loaded microparticles suspended within a bone cement, wherein the drug-loaded microparticles comprise at least one drug dispersed within a porous solid.

Also disclosed herein are methods of treating a bone disease by administering a composition comprising a plurality of drug-loaded microparticles suspended within a bone cement, wherein the drug-loaded microparticles comprise at least one drug dispersed within a porous solid.

The disclosed compositions may be provided as a composition ready for administration, as a drug-loaded microparticle that may need to be mixed with bone cement and formulated as, for example, described above prior to administration, or as an antibiotic that may need to be mixed with the porous solid and bone cement prior to administration. Kits and techniques to incorporate the drug, microparticle, and/or bone cement can be used as described in detail herein.

Bone diseases that may be treated may include, but are not limited to, arthroplasty (such as that of the hip and knee), osteomyelitis, and the like. Such bone diseases also include any tissue infection, including those that exhibit a poor blood supply such that systemic antibiotics are less effective.

In some embodiments, the drug may include an antibiotic, bone growth factors, chemotherapeutics, or any suitable biologically-active agent useful in treating an infection at the implant site, or a combination thereof. Examples of biologically-active agents include but are not limited to antiparasitic agents (such as quinacrine, chloroquine, quinine, and the like), antifungal agents (such as nystatin, amphotericin, miconazole, tolnaflate, undecyclic acid and its pharmaceutically acceptable salts, and the like), antiviral agents (such as vidarabine, acyclovir, ribarivin, amatine hydrochloride, iododeoxyuridine, dideoxyuridine, interferons, and the like). The antibiotic may include but is not limited to an aminoglycoside antibiotic, a glycopeptide antibiotic, a macrolide antibiotic, and a combination thereof. In some variations, the antibiotic may be gentamicin.

In some embodiments, the composition may be administered at a therapeutically effective dosage. The dosage may be dependent on the subject and disease state being treated, the severity of the affliction, the manner and schedule of administration and the judgment of the prescribing physician. The compositions may be administered such that the delivery of the drug is localized to the site of disease, such as the infected site. In some embodiments, the compositions may be administered within the infected joint space by surgically implanting the composition.

In some embodiments, after administration of the composition, the composition may release the drug. In some variations, the drug may be released at a sustained fashion over a prolonged period of time, such as 1 week, 2 weeks, 3 weeks, 4 weeks, 5 weeks, 6 weeks, 7 weeks, 8 weeks, or more. Some embodiments provide for up to 100% of drug release, up to about 90% of drug release, up to about 80% of drug release, up to about 70% of drug release, or up to about 60% of drug release.

The composition can be adapted to release said drug for a period of at least 14 days and can be adapted to release about 40 percent of the incorporated drug in 14 days. In some embodiments, the drug can be released for a period of 14 days (or about 14 days) to 70 days (or about 70 days). In some embodiments, the amount of incorporated drug to be released in the two week period can range from 40 percent (or about 40 percent) to 80 percent (or about 80 percent). The drug release period of time as well as the percentage of loaded drug that is released within a given drug release period are not particularly limiting and can be varied to meet different clinical demands. For example, the drug release period can vary from hours to months. Likewise the percentage of drug released during the period can vary from less than about 10% to at least about 90% by weight.

In some embodiments, a sufficient amount of drug, such as antibiotic, is released such that the infection is cured. In some embodiments, a sufficient amount of drug, such as an antibiotic is released to cure a bone disease and/or alleviate the symptoms associated with such disease.

In some embodiments, the compositions, such as those having antibiotics as the at least one drug, may maintain much higher cytotoxic levels of drugs, particularly antibiotics, for much longer than the currently available methods. Thus, cure rates may be substantially improved and the need for systemic antibiotics may be decreased.

"Treat," "treatment," or "treating," as used herein refers to administering a compound or pharmaceutical composition to a subject for prophylactic and/or therapeutic purposes. Subject" as used herein, means a human or a non-human mammal, e.g., a dog, a cat, a mouse, a rat, a cow, a sheep, a pig, a goat, a non-human primate or a bird, e.g., a chicken, as well as any other vertebrate or invertebrate.

The term "mammal" is used in its usual biological sense. Thus, it specifically includes, but is not limited to, primates, including simians (chimpanzees, apes, monkeys) and humans, cattle, horses, sheep, goats, swine, rabbits, dogs, cats, rodents, rats, mice guinea pigs, or the like.

An "effective amount" or a "therapeutically effective amount" as used herein refers to an amount of a therapeutic agent that is effective to relieve, to some extent, or to reduce the likelihood of onset of, one or more of the symptoms of a disease or condition, and includes curing a disease or condition. "Curing" means that the symptoms of a disease or condition are eliminated; however, certain long-term or permanent effects may exist even after a cure is obtained (such as extensive tissue damage).

EXAMPLES

The following Examples are presented for the purpose of illustration and should not be construed as limitations.

Example 1: Incorporation of Gentamicin in 90 mm×9 mm Rods

Drug-loaded microparticles were prepared by dissolving gentamicin, an exemplary antibiotic, in water and adding silica microparticles (Sipernat 50s silica microparticles with a mean particle size 7.5 µm, Evonik Industries, Frankfurt am Main, Germany). The resultant suspension was equilibrated for 2 hours, and the aqueous vehicle was then removed by lyophilization. The resultant non-erodible silica/gentamicin powder was then sieved through a 100 µm mesh to remove aggregates, and had a final gentamicin loading of 50% w/w. Compositions in the shape of microcomposite rods were prepared by mixing 30% w/w of the non-erodible silica/gentamicin microparticle powder with 70% w/w of SIMPLEX® orthopedic cement powder, so that the final gentamicin loading was 15% w/w, the same concentration as in the control rods. The blended powders were then mixed with the methacrylate liquid component, and the resultant dough pressed into the 90 mm×9 mm delrin molds and allowed to cure for at least 24 hours. After curing, release testing was performed by placing rods in 500 mL of release media (0.1% polysorbate 80 in nanopure water) at 37° C. which was continuously stirred at 100 rpm. At each time point, the receiver fluid was completely removed from each station and replaced with fresh solution. Gentamicin concentration was measured by reverse phase HPLC.

For comparison, control rods were prepared by mixing SIMPLEX® orthopedic cement powder (a PMMA-based cement) with gentamicin powder (to a final drug loading of 15% w/w). After blending the powders, they were then mixed with the commercial (SIMPLEX®) liquid methacrylate monomer. The resultant dough was then pressed into a 90 mm×9 mm rod-shaped delrin mold and allowed to cure for at least 24 hours.

As seen in FIG. 1, rods comprised of only orthopedic PMMA-based cement and gentamicin released only a small fraction of their payload as a burst over the first 24 hours of testing, after which there was little further release of drug. The microcomposite rods, on the other hand, provided a significantly improved release profile, releasing 80% of their entire incorporated drug payload in a sustained fashion of up to four weeks duration.

The strength of materials is usually investigated through compressive, tensile, or shear tests. Materials are generally stronger in compression than tension and the weakest in shear because micro and/or macro-structural flaws in the material may be the most detrimental in tension and shear compared to compression. The compression test is more common, because experimental setup and specimen preparation can be simpler and the test can generate more favorable data. In comparison, tension and shear tests may require more sophisticated experimental setup and specimen preparation and are vulnerable against internal flaws and imperfections in the fixturing. Additional mechanical property assessments (such as compressive strength, shear strength, bending strength, hardness, fatigue, creep, and the like) can be done for further detailed description of the material. Specimen geometry can be also modified to see whether sample preparation (such as voids during in making rods, curing rate and temperature gradient in the molds, etc.) has any effect on the results.

Figure 3:
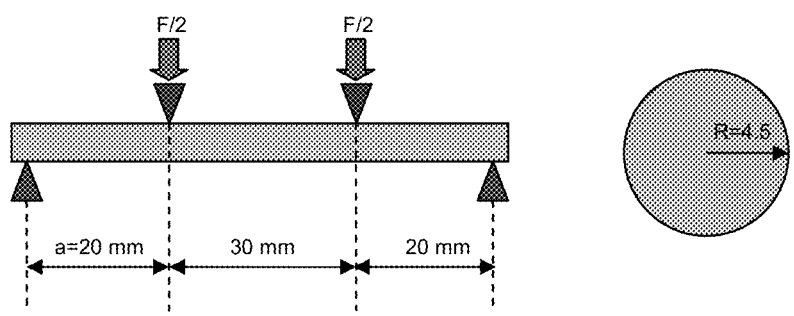
FIG. 3 depicts a schematic depicting how a bending test may be carried out.

Samples from each group were reserved for mechanical strength assessment both before and after elution testing. For testing, each sample was placed in a custom-made four-point bending fixture as illustrated in FIG. 3. This setup is described previously in the literature and ASTM standards. Briefly, each sample rod (~90 mm) was horizontally positioned on the bottom fixture providing support at two points 70 mm apart. The top fixture was used to apply loading to the sample at two points (30 mm apart) within the span of bottom support points. Samples were loaded at a rate of 5 mm/min until fracture. The maximum load borne by the sample was used to calculate the strength.

Figure 2:
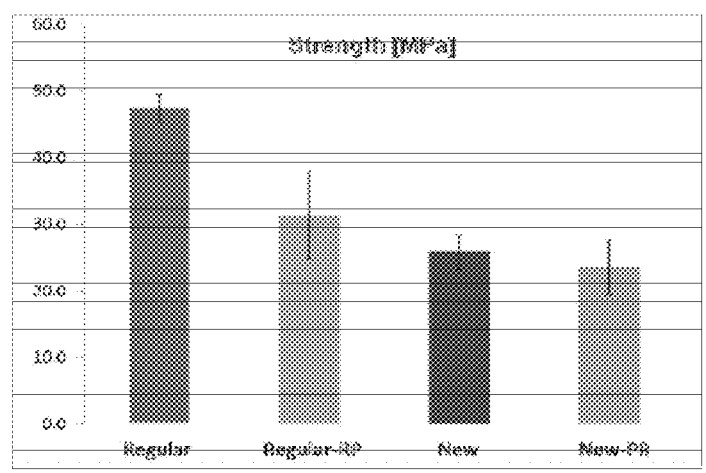
FIG. 2 depicts a graph showing the comparison of strength of cement rods obtained from commercially available formulation ("Regular") and an exemplary formulation as disclosed herein ("New") and tested before or after ("—PR," post release) drug release test. Note that the loss of strength in regular cement after drug release was significantly higher compared to the new formulation. The strength of New cement rods was less than the regular cement but was deemed sufficient for particular orthopedic applications.

As shown in FIG. 2, the results of the strength testing showed that the cement rods of the disclosed formulation (New) maintained the original strength after the release of the porosigens (New-PR), whereas commercially available cement formulations (Regular) showed a significant loss in strength after drug elution (Regular-PR). The initial strength of the exemplary formulation of the disclosed invention was less than the regular cement; however, it is deemed acceptable for certain orthopedic applications.

As illustrated in FIG. 3, a four-point bending test as recommended in the ASTM and ISO standards was also used to evaluate the bending modulus of the disclosed compositions before and after release of the drug. The bending test can be a simpler setup than a tension test. The bending test also can still evaluate the sample for its capacity against tensile stress because, in a bending test, one side of the sample is subject to compression and the opposite side is subject to tension, where the initial failure starts. For testing, samples shaped in 9×90 mm cylindrical rods were positioned in a four-point bending apparatus. The rods were supported at two terminal points with 70 mm distance at the bottom and forced to bend at two points with 30 mm separation at the top (FIG. 3). The bending modulus was calculated using the highest load encountered at the full fracture of the specimen. The formula used in these calculations was as follows:

$$\text{Bending Modulus: } E = \frac{Fa^2}{6\delta I}(3L - 4a)I = \frac{\pi R^4}{4}$$

Where F is the maximum load, a is the moment arm, R is the radius, I is the moment of inertia of the cross-sectional area, $\delta$ is the deflection at an L, the effective length (i.e., span between bottom supports).

Samples tested included commercially available SIMPLEX® loaded with 15% gentamicin before and after 8 weeks of an in vitro elution experiment and an exemplary formulation of the disclosed compositions loaded with 15% gentamicin before and after 8 weeks of an in vitro elution experiment.

Figure 4:
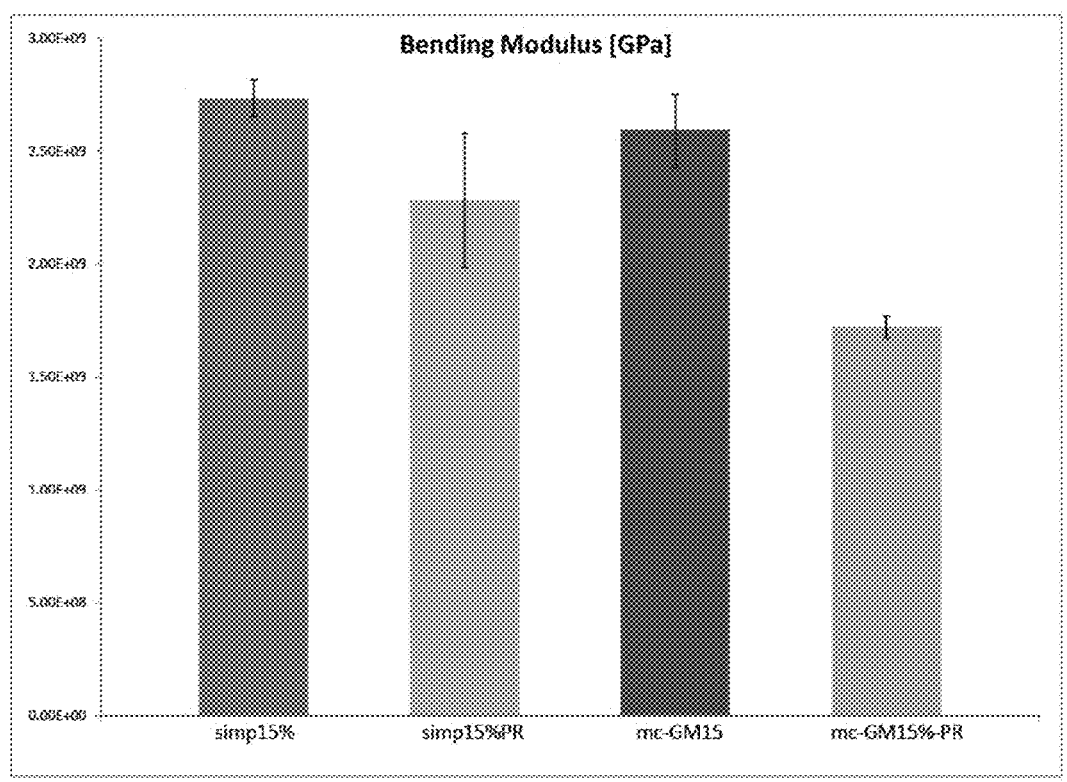
FIG. 4 depicts a graph showing the comparison of results obtained from bending tests of SIMPLEX® formulations having 15% gentamicin ("simp15%") and an exemplary formulation of the disclosed invention ("mc-GM15"). Results of the SIMPLEX® formulations and the exemplary formulation post-release of drug are also shown ("simp15% PR" and "mc-GM15%-PR," respectively).

FIG. 4 depicts a graph showing the comparison of results obtained from bending tests of SIMPLEX® formulations having 15% gentamicin ("simp15%") and an exemplary formulation of the disclosed invention ("mc-GM15"). Results of the SIMPLEX® formulation and the exemplary formulation post-release of drug are also shown ("simp15% PR" and "mc-GM15%-PR," respectively). The results show that the bending modulus of the disclosed formulations before and after drug release may be deemed acceptable for orthopedic applications. The difference between the commercially available formulations (where the results are in agreement with literature) and the disclosed formulations may be deemed to be reasonable. Moreover, the bending modulus of the disclosed formulation may be within similar range as formulations reported by Shen et al.

Example 2: Incorporation of Gentamicin and, Separately, the Incorporation of Vancomycin into 10 mm×6 mm Rods Drug-loaded microparticles containing either vancomycin or gentamicin were prepared by dissolving the drug in water and adding silica microparticles (Sipernat 50s silica microparticles with a mean particle size 7.5 μm, Evonik Industries, Frankfurt am Main, Germany). The resultant suspensions were equilibrated for 2 hours, and the aqueous vehicle was then removed by lyophilization. The resultant non-erodible silica/drug powders were then sieved through a 100 μm mesh to remove aggregates, and had a final drug loading of 50% w/w. Compositions of the disclosed invention in the shape of microcomposite rods were prepared by mixing 30% w/w of the non-erodible silica/drug microparticle powders with 70% w/w of SIMPLEX® orthopedic cement powder, so that the drug loading in the powder component was 15% w/w, the same concentration as in the control rods. The blended powders were then mixed with the methacrylate liquid component so that the final dough consisted of 10% by weight of drug, 10% w/w silica, 48% w/w PMMA cement, and 32% w/w methacrylate monomer. The resultant dough was pressed into 10 mm×6 mm Teflon molds and allowed to cure for at least 24 hours. After curing, release testing was performed by placing rods in 500 mL of release media (50 mM Tris buffer, pH 7.6) at 37° C. which was continuously stirred at 100 rpm. At each time point, the receiver fluid was completely removed from each station and replaced with fresh solution. Vancomycin concentration was measured by reverse phase HPLC.

For comparison, control rods were prepared by mixing SIMPLEX® orthopedic cement powder (a PMMA-based cement) with either gentamicin or vancomycin powder to obtain a drug loading in the powder component of 15% w/w. After blending the powders, they were then mixed with the commercial (SIMPLEX®) liquid methacrylate monomer to form a dough containing 10% w/w drug, 58% w/w PMMA cement, and 32% w/w methacrylate monomer. The resultant dough was then pressed into a 10 mm×6 mm rod-shaped Teflon mold and allowed to cure at ambient temperature for at least 24 hours.

As seen in FIG. 5 and Table 1 below, the control rods comprised of only orthopedic PMMA-based cement and drug released a small fraction of their payload as a burst over the first 24 hours of release testing, after which there was a significant decline in the release rate of drug. The microcomposite rods, on the other hand, provided a significantly improved release profile, wherein 50% or more of the device payload of drug was released in 20 days or less, the remainder being released in a sustained fashion for up to 70 days.

TABLE 1

Release rates of gentamicin and vancomycin (normalized to the surface area of each device, expressed in $mm^2$) from microparticle-based microcomposite rods and from polymethylmethacrylate-based cement (control) rods.

| | Day 1 Release Rate (mcg/$mm^2$/day) | Day 4 Release Rate (mcg/$mm^2$/day) | Day 7 Release Rate (mcg/$mm^2$/day) | Day 10 Release Rate (mcg/$mm^2$/day) | Day 14 Release Rate (mcg/$mm^2$/day) |
|---|---|---|---|---|---|
| Gentamicin microparticle-based microcomposite rod | 33.16 ± 2.38 | 5.67 ± 1.13 | 3.66 ± 0.50 | 2.43 ± 0.17 | 3.13 ± 0.69 |
| Gentamicin PMMA cement | 6.83 ± 1.51 | 0.32 ± 0.2 | 0.20 ± 0.06 | 0.16 ± 0.05 | 0.16 ± 0.08 |
| Vancomycin microparticle-based microcomposite rod | 15.29 ± 1.98 | 2.51 ± 0.46 | 1.79 ± 0.33 | 1.20 ± 0.23 | 0.84 ± 0.08 |
| Vancomycin PMMA cement | 5.47 ± 0.33 | 0.28 ± 0.04 | 0.24 ± 0.08 | 0.15 ± 0.02 | 0.11 ± 0.01 |

Various numerical examples, tables, graphs, and data are presented herein. These numerical examples, tables, graphs, and data are intended to illustrate certain example embodiments and not intended to limit the scope of the disclosed apparatus and methods.

The various features, compositions, and methods described above may be used independently of one another, or may be combined in various ways. All possible combinations and subcombinations are intended to fall within the scope of this disclosure. In addition, certain method or process blocks may be omitted in some implementations. The methods and processes described herein are also not limited to any particular sequence or order, and the blocks or operations relating thereto can be performed in other sequences or orders that are appropriate. For example, described blocks or operations may be performed in an order other than that specifically disclosed, or multiple blocks or operations may be combined in a single block or operation. The example blocks or operations may be performed in serial, in parallel, or in some other manner. Blocks or operations may be added to, removed from, or rearranged compared to the disclosed example embodiments. The example systems and components described herein may be configured differently than described. For example, elements may be added to, removed from, or rearranged compared to the disclosed example embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

What is claimed is:

1. A composition, comprising a drug-loaded microparticle comprising at least one drug and a porous ceramic, wherein the drug-loaded microparticle has a random, non-arrayed pore structure into which the at least one drug is embedded, wherein the drug-loaded microparticle is dispersed in a bone cement, and wherein the porous ceramic comprises silica.

2. The composition of claim 1, wherein the at least one drug is an antibiotic, a bone growth factor, a chemotherapeutic, or a combination thereof.

3. The composition of claim 2, wherein the antibiotic is an aminoglycoside antibiotic, a glycopeptide antibiotic, a macrolide antibiotic, fluoroquinolones, sulfa, tetracycline, rifampin, vancomycin, cephalosporin, penicillin, or a combination thereof.

4. The composition of claim 2, wherein the antibiotic is gentamicin.

5. The composition of claim 1, comprising a plurality of drug-loaded microparticles, wherein the drug-loaded microparticles have a mean particle size of about 2 μm to about 200 μm.

6. The composition of claim 1, wherein the bone cement is a polymethylmethacrylate-based bone cement.

7. The composition of claim 1, wherein the amount of the at least one drug that is embedded in the drug-loaded microparticle is from about 1% to about 70% by weight of the drug to weight of the drug-loaded microparticle.

8. The composition of claim 1, wherein the amount of the at least one drug that is embedded in the drug-loaded microparticle is less than about 40% by weight of the drug to weight of the drug-loaded microparticle.

9. The composition of claim 1, wherein the weight ratio of the drug-loaded microparticle to the bone cement is about 1:9 to about 7:3.

10. A method of treating a bone condition, comprising locally administering a composition comprising a drug-loaded microparticle comprising at least one drug and a porous ceramic, wherein the drug-loaded microparticle has a random, non-arrayed pore structure into which the at least one drug is embedded, wherein the drug-loaded microparticle is dispersed within a bone cement, and wherein the porous ceramic comprises silica.

11. The method of claim 10, wherein the bone condition is an infected joint space.

12. The method of claim 10, wherein the at least one drug is selected from an antibiotic, a bone growth factor, or a chemotherapeutic, or a combination thereof.

13. The method of claim 10, wherein locally administering the composition comprises surgically implanting the composition.

14. The method of claim 10, wherein locally administering the composition comprises injecting the composition.

15. The method of claim 10, wherein the at least one drug is released over a period of 14 days to 70 days.

16. The method of claim 10, wherein 40 percent to 80 percent of the at least one drug is released.

17. The method of claim 10, wherein 40 percent of the at least one drug is released over a period of 14 days.

* * * * *